US010551467B2

(12) United States Patent
Beck

(10) Patent No.: US 10,551,467 B2
(45) Date of Patent: Feb. 4, 2020

(54) METHOD AND APPARATUS FOR MOVEMENT COMPENSATION DURING MAGNETIC RESONANCE IMAGING

(71) Applicant: Siemens Aktiengesellschaft, Munich (DE)

(72) Inventor: Thomas Beck, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 387 days.

(21) Appl. No.: 15/135,763

(22) Filed: Apr. 22, 2016

(65) Prior Publication Data
US 2016/0313433 A1    Oct. 27, 2016

(30) Foreign Application Priority Data

Apr. 24, 2015    (DE) .......................... 10 2015 207 590

(51) Int. Cl.
*G01R 33/567*    (2006.01)
*G01R 33/565*    (2006.01)
(Continued)

(52) U.S. Cl.
CPC .......... *G01R 33/5676* (2013.01); *A61B 5/055* (2013.01); *G01R 33/5611* (2013.01); *G01R 33/56509* (2013.01)

(58) Field of Classification Search
CPC ............ G01R 33/4853; G01R 33/5676; G01R 33/5611; G01R 33/4824; G01R 33/482;
(Continued)

(56) References Cited

U.S. PATENT DOCUMENTS

2002/0180436 A1* 12/2002 Dale ................ G01R 33/56509
324/307
2004/0039276 A1*  2/2004 Ikezaki .............. G01R 33/5611
600/407
(Continued)

FOREIGN PATENT DOCUMENTS

WO    WO-2015/052002 A1    4/2015
WO    WO-2015052002 A1 *  4/2015

OTHER PUBLICATIONS

Tisdall, M. D., Hess, A. T., Reuter, M., Meintjes, E. M., Fischl, B., & van der Kouwe, A. J. (2012). Volumetric navigators for prospective motion correction and selective reacquisition in neuroanatomical MRI. Magnetic resonance in medicine, 68(2), 389-399. (Year: 2012).*
(Continued)

*Primary Examiner* — Bill Thomson
*Assistant Examiner* — Johnathan Maynard
(74) *Attorney, Agent, or Firm* — Schiff Hardin LLP

(57) ABSTRACT

In a magnetic resonance apparatus and operating method therefor, movement compensation during raw data acquisition is accomplished by operating the data acquisition scanner to acquire data from a reference navigator volume at a first point in time, using a simultaneous multi-slice technique with a first acceleration factor and a first number of first slice groups, and to acquire data from a navigator volume at a second point in time, also using a simultaneous multi-slice technique, but with a second acceleration factor and a second number of second slice groups, with the first and second acceleration factors being equal. Movement information is determined from the reference navigator volume and the navigator volume, describing movement of the patient occurring between the first and second points in time. Data acquisition parameters of the scanner are set after (Continued)

the second point in time, dependent on the movement information, for acquiring further magnetic resonance data.

13 Claims, 2 Drawing Sheets

(51) Int. Cl.
*A61B 5/055* (2006.01)
*G01R 33/561* (2006.01)

(58) Field of Classification Search
CPC .............. G01R 33/5616; G01R 33/561; G01R 33/20–64; A61B 6/113; A61B 6/7207; A61B 5/11; A61B 5/055–0565
USPC .................................................. 600/410–423
See application file for complete search history.

(56) References Cited

U.S. PATENT DOCUMENTS

| | | | | |
|---|---|---|---|---|
| 2012/0002858 | A1* | 1/2012 | Huang | G01R 33/5611 382/131 |
| 2012/0286777 | A1* | 11/2012 | Frost | G01R 33/56341 324/307 |
| 2013/0187649 | A1* | 7/2013 | Bhat | A61B 5/055 324/307 |
| 2013/0229177 | A1* | 9/2013 | Bammer | G01R 33/56341 324/309 |
| 2013/0278263 | A1* | 10/2013 | Huang | G01R 33/5611 324/309 |
| 2015/0084629 | A1 | 3/2015 | Porter | |
| 2015/0323637 | A1* | 11/2015 | Beck | G01R 33/4828 600/410 |
| 2016/0047876 | A1* | 2/2016 | Alhamud | G01R 33/5616 324/309 |
| 2016/0266225 | A1* | 9/2016 | Johnson | G01R 33/56358 |

OTHER PUBLICATIONS

Porter, D. A., & Heidemann, R. M. (2009). High resolution diffusion-weighted imaging using readout-segmented echo-planar imaging, parallel imaging and a two-dimensional navigator-based reacquisition. Magn Reson Med, 62(2), 468-475. (Year: 2009).*

Sheltraw, D., Inglis, B., Deshpande, V., & Trumpis, M. (2012). Simultaneous reduction of two common autocalibration errors in grappa epi time series data. arXiv preprint arXiv:1208.0972. (Year: 2012).*

Tisdall, M. D., Hess, A. T., Reuter, M., Meintjes, E. M., Fischl, B., & van der Kouwe, A. J. (2012). Volumetric navigators for prospective motion correction and selective reacquisition in neuroanatomical MRI. Magnetic resonance in medicine, 68(2), 389-399. (Year: 2012).*

Lin, W., Nielsen, T., Qin, Q., Mostofsky, S. H., Wei, J., Huang, F., & Duensing, G. R. (2013). Real-time motion correction in two-dimensional multislice imaging with through-plane navigator. Magnetic resonance in medicine, 71(6), 1995-2005. (Year: 2013).*

Frost, R., Jezzard, P., Porter, D. A., Tijssen, R., & Miller, K. (2013). Simultaneous multi-slab acquisition in 3D multi-slab diffusion-weighted readout-segmented echo-planar imaging. In Proceedings of the 21st Annual Meeting of ISMRM, Salt Lake City, Utah, USA. (Year: 2013).*

Frost, R., Miller, K. L., Tijssen, R. H., Porter, D. A., & Jezzard, P. (2013). 3D multi-slab diffusion-weighted readout-segmented EPI with real-time cardiac-reordered k-space acquisition. Magnetic resonance in medicine, 72(6), 1565-1579. (Year: 2013).*

Frost, R., Miller, K. L., Porter, D. A., Tijssen, R. H., & Jezzard, P. (2013). 3D Multi-Slab Diffusion-Weighted Readout-Segmented Echo-Planar Imaging With Real-Time Cardiac-Reordered K-Space Acquisition. In Proceedings of the 21th Annual Meeting of ISMRM, Salt Lake City, Utah, USA. (Year: 2013).*

Skare, S., Hartwig, A., Mårtensson, M., Avventi, E., & Engström, M. (2014). Properties of a 2D fat navigator for prospective image domain correction of nodding motion in brain MRI. Magnetic resonance in medicine, 73(3), 1110-1119. (Year: 2014).*

Thesen et al: "Prospective Acquisition Correction for Head Motion With Image-Based Tracking for Real-Time fMRI" Magnetic Resonance in Medicine 44, pp. 457-465, (2000).

Thesen, Abstract of doctoral theses"Retrospective and Prospective Methods for Image-Based Correction of Patient Head Motions in Newuro-Functional Magnetic Resoannce Tomograpjy in Real-Time," Heidelberg University (2001).

Bhat et. al.: "EPI navigator based prospective motion correction technique for diffusion neuroimaging", Proc. Intl. Soc. Mag. Reson. Med. 20 p. 113 (2012).

Tisdall et al. :"MPRAGE Using EPI Navigators for Prospective Motion Correction", in: Proc. Intl. Soc. Mag. Reson. Med. 17, p. 4656, (2009).

Shankaranarayanan , et.al. :"Motion insensitive 3D imaging using a novel real-time image-based 3D PROspective MOtion correction method (3D PROMO)", Proc. Intl. Soc. Mag. Reson. Med., vol. 15, p. 2117, (2007).

Setsompop et.al.: "Blipped-Controlled Aliasing in Parallel Imaging for Simultaneous Multislice Echo Planar Imaging with Reduced g-Factor Penalty", in: Magnetic Resonance in Medicine, vol. 67, pp. 1210-1224, (first published online 2011); 2012.

MacLaren; "Prospective Motion Correction in Brain Imaging: A Review"; Magnetic Resonance in Medicine; vol. 69; pp. 621-636; (2013).

* cited by examiner

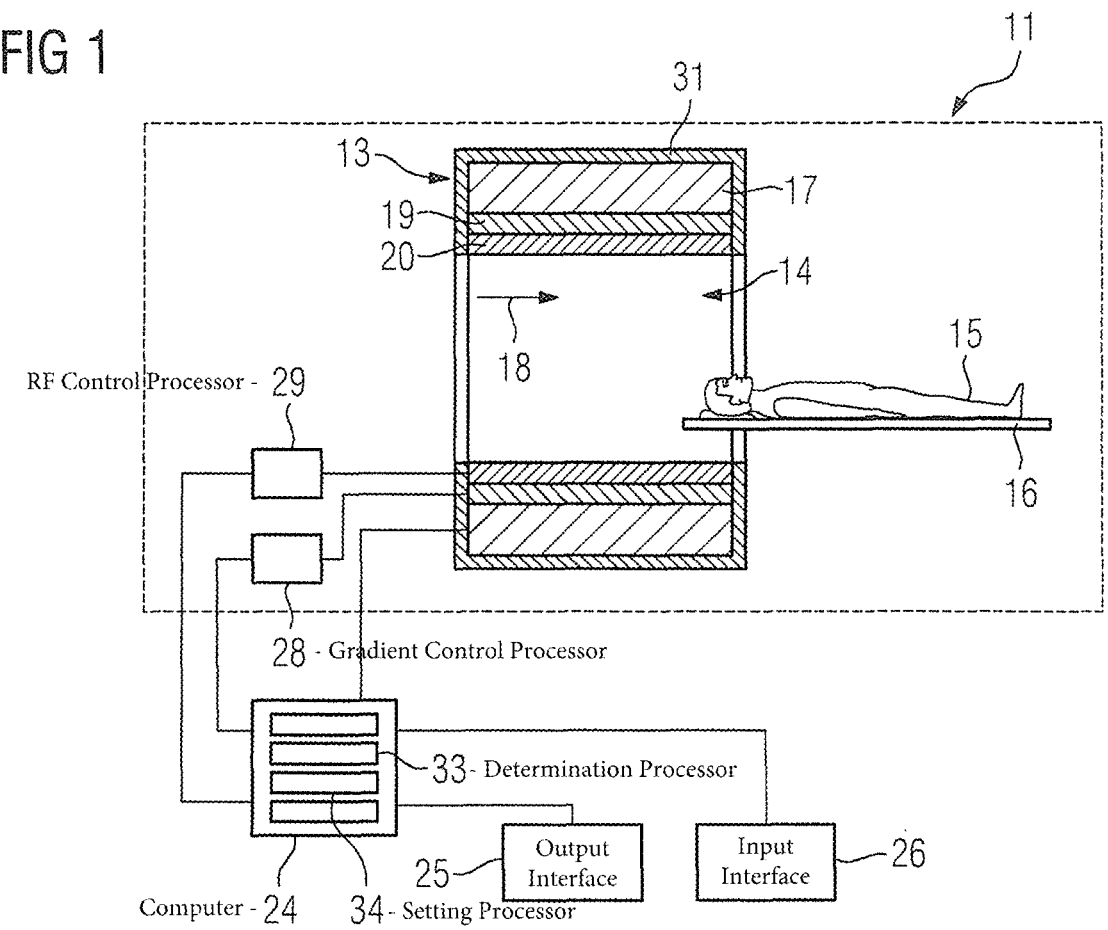
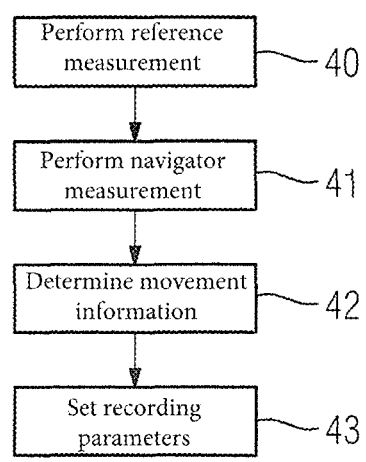

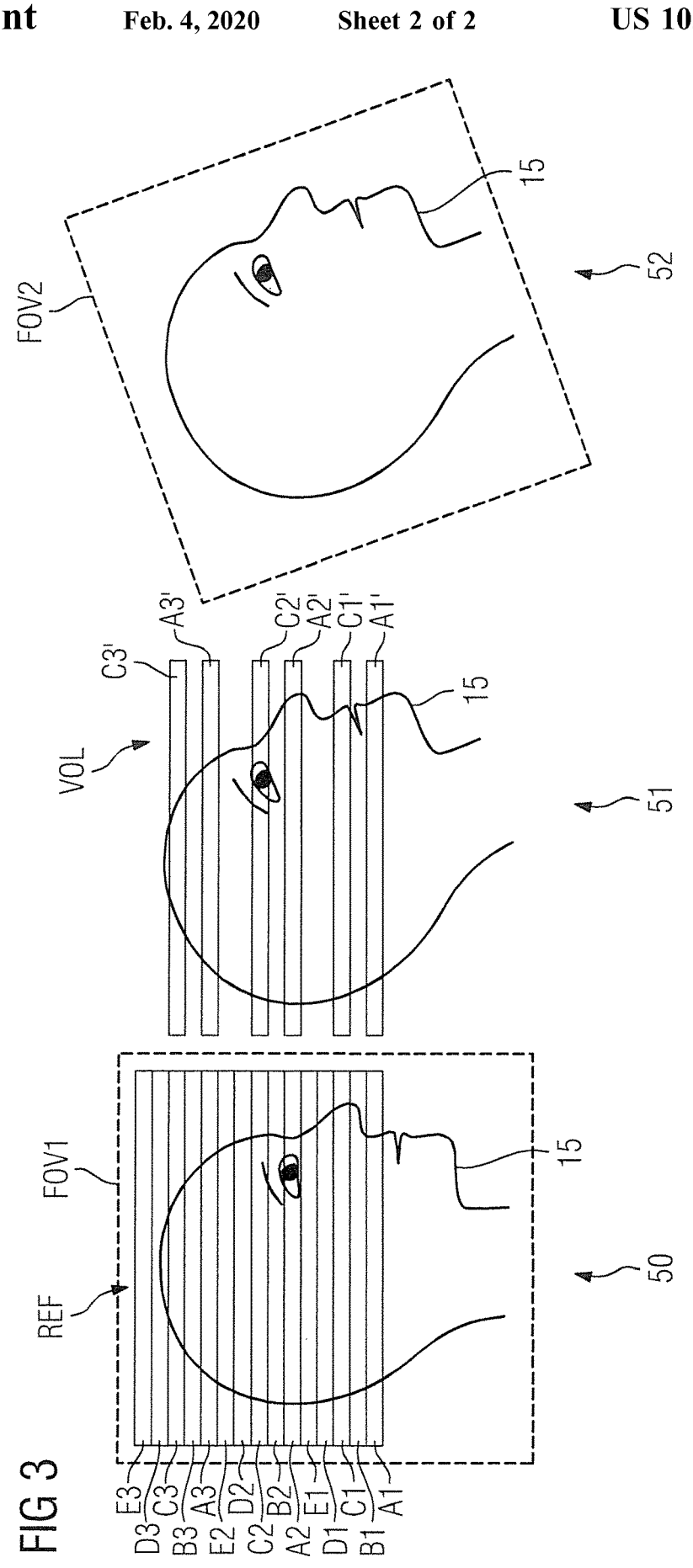

METHOD AND APPARATUS FOR MOVEMENT COMPENSATION DURING MAGNETIC RESONANCE IMAGING

BACKGROUND OF THE INVENTION

Field of the Invention

The invention concerns a method for movement compensation during magnetic resonance imaging, as well as a magnetic resonance apparatus and a non-transitory, computer-readable data storage medium for implementing such a method.

Description of the Prior Art

In a magnetic resonance apparatus, also referred to as a magnetic resonance tomography system, the body to be examined of a person to be examined, in particular a patient, is situated in a scanner of the apparatus, wherein the patient is subjected to a relatively high basic magnetic field, for example 1.5 or 3 or 7 tesla with the use of a main magnet. In addition, gradient fields are activated by the operation of gradient coils. Radio-frequency pulses, for example excitation pulses, are then emitted via a radio-frequency antenna arrangement by suitable antennas, causing the nuclear spins of certain atoms resonantly excited by these radio-frequency pulses to be tilted by a defined flip angle with respect to the magnetic field lines of the basic magnetic field. During the relaxation of the nuclear spins, radio-frequency signals, so-called magnetic-resonance signals are emitted and are received by suitable radio-frequency antennas, and then processed further. Finally, the desired image data can be reconstructed from the raw data acquired in this manner.

Therefore, for a specific measurement, a specific magnetic resonance sequence, also referred to as a pulse sequence, is implemented, which is composed of a series of radio-frequency pulses, for example excitation pulses and refocusing pulses, and gradient pulses to be emitted, which are suitably coordinated thereto, in different gradient axes along different spatial directions. Chronologically coordinated therewith, readout windows are set that predetermine the periods of time in which the induced magnetic resonance signals are acquired.

During magnetic resonance imaging, movement of the examination object can take place. For example, respiratory movement and/or heart movement of the examination object can occur. It is also possible for arbitrary movements of limbs of the examination object to occur. This movement of the examination object can result in an unwanted change to the magnetic resonance image data acquired during the magnetic resonance imaging, leading to motion artifacts in the magnetic resonance image data acquired. The movement can also reduce the quality of the magnetic resonance image data acquired.

Different methods are known for at least partial compensation of such movement of the examination object during magnetic resonance imaging. One known method is retrospective motion correction, which typically compensates the movement of the examination object in the magnetic resonance image data that are reconstructed, following the acquisition of the magnetic resonance raw data.

A further known method for at least partial compensation of the movement of the examination object is prospective motion correction. Prospective motion correction generally includes the detection and correction of a movement of the examination object during the actual acquisition of the magnetic resonance raw data. At the same time, in specific cases, prospective motion correction can take place in real time, or close to real time. Prospective motion correction can also include the determination of motion parameters characterizing a movement made by the examination object following the acquisition of a first part of the magnetic resonance raw data. It is then possible for recording parameters, for example a slice selection and/or a slice orientation for the acquisition of a second part of the magnetic resonance image data to be set using the motion parameters. This enables the acquisition of the magnetic resonance raw data to be adapted to the movement of the examination object during the actual magnetic resonance imaging.

One known possibility for prospective motion correction is the use of image-based navigators during the magnetic resonance raw data acquisition. This can be used particularly advantageously when the magnetic resonance raw data acquisition is performed using a magnetic resonance sequence with a long acquisition duration and/or with lengthy waiting times or dead times during the measurement, during which raw data representing a navigator volume can be acquired. In this case, the acquisition of a navigator volume typically entails the activation of radio-frequency pulses and the reading out of magnetic resonance measurement data in addition to the sequence elements used by the magnetic resonance sequence to record the diagnostic magnetic resonance raw data. The acquired data representing navigator volume are typically used only for prospective motion correction and can be discarded following the conclusion of the magnetic resonance sequence.

SUMMARY OF THE INVENTION

An object of the invention is to improve prospective compensation for movement of an examination object during magnetic resonance imaging.

The method according to the invention for movement compensation during magnetic resonance imaging of an examination object by means of a magnetic resonance (MR) apparatus includes the following method steps. The MR scanner is operated to execute a reference measurement at a first point in time during the magnetic resonance raw data acquisition, wherein MR data representing a reference navigator volume are acquired using a simultaneous-multi-slice technique with a first acceleration factor and a first number of first slice groups.

The MR scanner is operated to perform a navigator measurement at a second point in time during the magnetic resonance raw data acquisition, wherein MR data representing a navigator volume are acquired using a simultaneous multi-slice technique with a second acceleration factor and a second number of second slice groups, with the second acceleration factor equal to the first acceleration factor.

In a computer provided with both sets of navigator data, movement information is determined from the reference navigator volume and the navigator volume, the movement information describing a movement of the examination object between the first point in time and the second point in time.

Recording (data acquisition) parameters are set by the computer, dependent on the movement information, after the second point in time for operating the MR scanner for the magnetic resonance raw data acquisition.

The examination object can be a patient, a training volunteer, an animal or a phantom. During magnetic resonance data acquisition, magnetic resonance raw data are acquired, which can be made available to a user on a display unit and/or stored in a database.

The magnetic resonance raw data acquisition is implemented by the execution of a magnetic resonance sequence for the acquisition of the magnetic resonance raw data. The reference measurement and the navigator measurement are then implemented as a part of this magnetic resonance sequence. The first point in time at which the reference measurement takes place can be a starting point in time of the reference measurement. The first point in time can occur in an initial time period of the magnetic resonance sequence, advantageously before any magnetic resonance raw data are acquired according to the magnetic resonance sequence. The second point in time at which the navigator measurement takes place can be a starting point in time of the navigator measurement. The second point in time occurs chronologically after the first point in time. Hence, the second point in time can occur between the acquisition portions of of the magnetic resonance raw data according to the magnetic resonance sequence.

The navigator measurement can be the acquisition of multiple navigator volumes respectively at multiple second point in times after the first point in time during the activation of the magnetic resonance sequence. This enables a number of items of movement information to be determined at different point in times during the course of the magnetic resonance sequence, and allows the recording parameters to be set a number of times respectively with reference to the multiple items of movement information during the magnetic resonance sequence. This enables dynamic reactions to the movement of the examination object during the magnetic resonance imaging. For example, it is conceivable for a navigator volume to be acquired at a defined point during each repetition time of the magnetic resonance sequence, which is repeated multiple times. For example, it is conceivable for in each case a navigator volume to be acquired between the inversion pulses and the readout block of each of the repetition intervals. This enables a number of navigator volumes to be acquired at a number of defined second point in times. Therefore, the term "a navigator measurement" or "a navigator volume" explicitly includes the acquisition of number of navigator volumes, possibly number a plurality of navigator measurements, during the magnetic resonance sequence.

As noted in the magnetic resonance sequence, a reference measurement is performed in order to acquire a reference navigator volume at the first point in time. In most cases, only one reference measurement is performed in order to acquire exactly one reference navigator volume at the first point in time. It is also possible for a number of reference navigator volumes to be acquired, for example at a number of first point in times. The reference navigator volume can also be formed as an average over two or more measurements. The reference navigator volume can be used as the basis for the prospective motion correction for the entire magnetic resonance raw data acquisition or the entire magnetic resonance sequence. Thus, the first point in time can be considered to be a reference point in time that can be used as a reference for a subsequently detected movement of the examination object. The reference navigator volume can be formed by a navigator volume first measured during the magnetic resonance sequence. In specific cases, the reference measurement can be repeated once more during the magnetic resonance raw data acquisition, i.e. for a further reference navigator volume to be acquired at a further first point in time during the magnetic resonance sequence.

According to the inventive procedure, the reference navigator volume should be acquired during the reference measurement using the simultaneous multi-slice (SMS) technique. This enables accelerated acquisition of the reference navigator volume. The simultaneous multi-slice technique is for example known from the following publication: Setsompop et al. "Blipped-controlled aliasing in parallel imaging for simultaneous multi-slice echo planar imaging with reduced g-factor penalty.", Magn Reson Med. 2012. 67(5): 1210-1224. The simultaneous multi-slice technique involves the simultaneous excitation of a number of slices of a measuring volume. The number of slices that are simultaneously excited are typically grouped in a slice group. The simultaneous multi-slice technique is typically characterized by an acceleration factor, also called a simultaneous multi-slice factor (SMS factor). The acceleration factor indicates how many slices are simultaneously excited in a slice group by one single radio-frequency pulse. The acceleration factor is an integer and, for accelerated measurements, is at least two. With an acceleration factor of one, the measurement corresponds to a conventional, sequential measurement. Typical acceleration factors are within a range of up to six and are dependent on an observed body region and/or coil geometry and/or a magnetic resonance sequence used. The magnetic resonance signals can then be read out simultaneously from the multiple slices, superimposed in k-space. The subsequent reconstruction of the individual slices then involves a separation of the simultaneously read-out magnetic resonance signals in relation to the multiple slices. The magnetic resonance signals can be separated by using a known slice separation method, such as a slice-GRAPPA method in the slice direction as noted in the aforementioned article by Setsompop et al. This enables the simultaneous multi-slice technique to be used to acquire a number of slices at the same time. There is an interleaved acquisition of the multiple slices in order to minimize any influence on spatially adjacent slices from chronologically sequential slice measurements (possible cross-talk).

The reference navigator volume can be composed of a number of first slices, which are grouped together to form first slice groups. In each first slice group of the multiple first slice groups, a number of first slices among the plurality of first slices is excited simultaneously by a radio-frequency pulse. Consequently, the radio-frequency pulse acts simultaneously on all the first slices of a first slice group. Here, the number of slices forming a first slice group of the multiple first slice groups corresponds to the first acceleration factor. Consequently, each radio-frequency pulse simultaneously excites a number of first slices corresponding to the first acceleration factor. The reference navigator volume is excited by a number of radio-frequency pulses corresponding to the first number of first slice groups. Each first slice group of the multiple first slice groups can have the same number of first slices. Consequently, the total number of first slices of the reference navigator volume corresponds to the product of the first acceleration factor and the first number of first slice groups.

The simultaneous acquisition of the multiple first slices enables the time required for the acquisition of the reference navigator volume to be significantly reduced. In this case, the time saving factor is approximately of the same order of magnitude as the first acceleration factor. This enables a saving of the measuring time for the reference measurement. The shorter measuring time can be invested in improved imaging parameters, for example a higher number of first slices and/or a higher resolution within the first slices. The accelerated acquisition of the reference navigator volume can also have the result that a possible movement of the examination object during the reference measurement can be avoided and/or reduced. The shorter acquisition duration for the reference scan can reduce a probability and/or a component of a movement of the examination object during the reference scan. This is, therefore, advantageous since the reference navigator volume represents the basis for the prospective motion correction for the entire magnetic resonance imaging. For example, a reference navigator volume that has been falsified by a movement of the examination object could have a negative influence on the entire magnetic resonance imaging, in particular the entire prospective motion correction.

The navigator volume can be composed of a number of second slices that are grouped together to form second slice groups. In each second slice group of the multiple second slice groups, a number of second slices of the multiple second slices is excited simultaneously by a radio-frequency pulse. Consequently, the radio-frequency pulse acts simultaneously on all second slices of a second slice group. Here, the number of slices in a second slice group of the multiple second slice groups corresponds to the second acceleration factor. Consequently, each radio-frequency pulse simultaneously excites a number of second slices corresponding to the second acceleration factor. The navigator volume is excited by a number of radio-frequency pulses corresponding to the second number of second slice groups. In this case, each second slice group of the multiple second slice groups has the same number of second slices. Consequently, the total number of second slices of the navigator volume corresponds to the product of the second acceleration factor and the second number of second slice groups. Advantageously, the same calibration scan can be used for the reconstruction of the reference navigator volume and navigator volume acquired by the simultaneous multi-slice technique.

Advantageously, the same acceleration factor can be used for both the performance of the reference measurement and the performance of the navigator measurement. In this way, the number of simultaneously excited first slices in the reference navigator volume is equal to the number of simultaneously excited second slices in the navigator volume. In another embodiment, the number of slice groups, and hence acquired slices, in the navigator volume is fewer compared to the reference navigator volume, as described in more detail below.

The simultaneous acquisition of the number of second slices enables the time required for the acquisition of the navigator volume to be significantly reduced. In this case, the time-saving factor is approximately of the same order of magnitude as the second acceleration factor. This enables a saving of the measuring time for the navigator measurement. The shorter measuring time can be invested in improved imaging parameters, for example a higher number of second slices and/or a higher resolution within the second slices. The shorter measuring time can advantageously have the result that a more accurate detection of the movement of the examination object by the navigator measurement is enabled. The shorter measuring time for the navigator measurement has the result that the navigator measurement, which is typically inserted in the magnetic resonance sequence actually used for the magnetic resonance imaging, causes less interference to the magnetic resonance sequence actually used. This is based on the consideration that the navigator measurement is typically inserted in dead times, which occur during the magnetic resonance sequence actually used for the magnetic resonance imaging. To this end, such dead times should typically be at least 150 ms, in particular at least 250 ms, in particular at least 500 ms.

In this case, the movement of the examination object can take place between the first point in time and the second point in time. For example, a respiratory movement and/or heart movement of the examination object can occur. Arbitrary movements of limbs of the examination object can also occur. The movement made by the examination object can be reflected in image contents of the navigator volume compared to image contents of the reference navigator volume. In this way, the movement information can be determined by a registration of the navigator volume to the reference navigator volume, for example. In this way, the movement information can characterize how the examination object has moved between the first point in time and the second point in time.

The detected movement information can be returned to the magnetic resonance sequence used for the magnetic resonance raw data acquisition so that, for the magnetic resonance imaging after the second point in time, the movement of the examination object can be at least partially compensated for the magnetic resonance raw data acquisition. For example, the movement information can be used to set the recording parameters for the magnetic resonance imaging after the second point in time such that the movement of the examination object can be counteracted. This enables a movement correction as a function of the movement information, in real time during the actual magnetic resonance imaging. A procedure of this kind is usually also called prospective motion correction.

Hence, the movement information can be determined particularly quickly from the reference navigator volume and the navigator volume, in particular a model-based assumption can be made for the movement information. The model-based assumption can embody motion parameters, which are formed by the movement information. Here, particularly advantageous is a rigid model-based assumption for the movement information, which has six motion parameters, namely three translation parameters and three rotation parameters. The use of a rigid model-based assumption has been found to be advisable particularly in the case of magnetic resonance imaging of the head of the examination object. This advantageously enables the recording parameters to be set with a high temporal resolution. Obviously, it is also possible for other model-based assumptions known to those skilled in the art to be made for the movement information, for example non-rigid model-based assumptions. The use of a non-rigid and/or non-linear movement model is advisable for regions of an image for which a rigid movement model-based assumption is not applicable. In the case of head-imaging, this can be, for example, a neck region and/or a jaw region and/or an eye socket region of the examination object.

The setting of the recording parameters as a function of the movement information can, for example, involve an adaptation of an imaging volume for the magnetic resonance imaging after the second point in time as a function of the movement information. In a rigid case, it is possible, for example, for slices of the imaging volume to be adapted for the magnetic resonance raw data acquisition after the second point in time with reference to the motion parameters, in particular the three translation parameters and three rotation parameters. This enables a change to the position and/or anatomy of the examination object caused by the movement, for example a tilting of the head of the examination object, to be directly compensated during the measurement. The adaptation of the imaging volume is in particular performed by means of an adaptation of gradient fields, which are activated during the magnetic resonance raw data acquisition after the second point in time, for example during excitation radio-frequency pulses and/or readout windows.

In this case, the setting of the recording parameters dependent on the movement information is performed with a time offset relative to the acquisition of the navigator volume. For example, it can be the case that initially at least one repetition time passes following the acquisition of a specific navigator volume at the second point in time until the recording parameters are used, which are adapted using the movement information, which is determined with reference to the navigator volume. This delay can be caused, for example, by the computing time required for the reconstruction of the navigator volume and/or the registration of the navigator volume to the reference navigator volume. However, the delayed movement compensation typically can be tolerated, particularly when there is a continuous and/or small movement of the examination object, such as a respiratory movement.

In another embodiment, the second number of second slice groups is smaller than the first number of first slice groups.

This reduces the number of acquired second slices of the navigator volume compared to the number of acquired first slices of the reference navigator volume. Thus the number of radio-frequency excitation pulses, which are used to excite the navigator volume, is smaller than a number of radio-frequency excitation pulses that are used to excite the navigator volume. In this embodiment, the second slice groups represent a subset of the first slice groups. In this way, different imaging parameters are used for the reference measurement and the navigator measurement. In this case, the second number of second slice groups can be dynamically varied for different navigator volumes, which are acquired at different second point in times. The variation of the second number of second slice groups can, for example, be performed in dependence on the available dead times of the magnetic resonance sequence actually used for the acquisition of the magnetic resonance measurement data. In this case, the resolution of the measured data of the different navigator volumes in the slice planes (in-plane resolution) is advantageously kept constant.

The reduction in the number of second slice groups compared to the number of first slice groups advantageously reduces the time required for the navigator measurement still further. This enables an even quicker detection of the movement of the examination object. Alternatively, even though the number of second slice groups in the navigator volume is reduced, a constant acquisition time can be maintained, so a higher resolution of the measured data of the navigator volume in the slice planes (in-plane resolution) can be achieved. A higher in-plane resolution with a reduction in the number of slices can be more advantageous for the determination of the movement information than an isotropic navigator volume with reduced in-plane resolution. Simultaneously, the reduction in the number of second slice groups enables the second slice groups to be selected such that the second slices of the navigator volume are spatially as far apart from each other as possible. This enables a robust detection of the movement of the examination object using the navigator volume and the reference navigator volume.

The reference navigator volume can also include the complete anatomy of the examination object, preferably in isotropic resolution. Despite a reduced number of slices in the navigator volume, this enables a precise registration of the navigator volume to the reference navigator volume for the determination of the movement information, even in the case of a movement of the examination object. Therefore, increased scanning of the anatomy of the examination object in the reference measurement is possible, since the reference measurement typically causes little interference to the magnetic resonance sequence actually used for the acquisition of the magnetic resonance measurement data. For example, the entire reference measurement can be performed before the actual acquisition of the magnetic resonance measurement data.

In another embodiment, the second number of second slice groups is less than half the size of the first number of first slice groups. This enables an acceleration of the navigator measurement.

In another embodiment, the second slice groups represent a subset of the first slice groups. Thus, all second slice groups of the navigator volume are already acquired in the reference navigator volume. This enables a comparison, for example a registration, of the navigator volume and the reference navigator volume for the determination of the movement information.

In another embodiment, the second slice groups are selected such that the imaging volume covered by the navigator volume is substantially the same size as the reference navigator volume, but the resolution of the navigator volume in the slice direction is lower than the resolution of the reference navigator volume in the slice direction. Preferably, a dimension of the navigator volume in the slice direction is of a similar size, namely a maximum two slice thicknesses of the reference navigator volume smaller, most preferably the same size as a dimension of the navigator volume. In this case, the navigator volume can cover the reference navigator volume to a large degree. Approximately uniform coverage is advantageous. The uniform coverage of the reference navigator volume by the navigator volume and/or the corresponding sizes of the navigator volume and the reference navigator volume achieves the advantage that robust detection of the movement from the navigator volume and the reference navigator volume is possible. Preferably, the second slice groups are selected simultaneously such that the number of second slices in the navigator volume are positioned as far away as possible from one another, as will be described in more detail below. This enables the second slice groups, which are excited for the acquisition of the navigator volume, to be selected in a manner designed to achieve a particular result or goal.

In another embodiment, the reference navigator volume has a number of first slices that are grouped together to form the first slice groups, and the navigator volume has a number of second slices that are grouped together to form the second slice groups. In this embodiment, the grouping of the first slices to form the first slice groups and the grouping of the second slices to form the second slice groups is performed using the simultaneous and/or coherent excitation of the slices according to the simultaneous multi-slice technique. In this way, the first slices of the number of first slice groups which are grouped to form a first slice group are those that are simultaneously excited. Also, the second slices of the number of second first slice groups which are grouped to form a second slice group are those that are simultaneously excited.

In another embodiment, the second slice groups are selected such that the positioning of the number of second slices in the navigator volume is as far apart as possible from one another. The second slices can most advantageously be positioned as far away as possible from one another in the navigator volume. This enables a uniform coverage of the reference navigator volume by the navigator volume. It is thereby possible to avoid specific adjacent second slices of the number of second slices from being positioned closer to one another than other adjacent second slices of the number of second slices. The positioning of the number of second slices with the greatest possible interslice distance achieves the advantage that the separation of simultaneously excited second slices of the number of second slices during the reconstruction of the navigator volume is particularly simple. In addition, increasing the spatial distance between chronologically sequential excited slice groups implicitly minimizes any mutual influence of the slices due to crosstalk. This enables the separation of the second slices that are simultaneously excited by the simultaneous multi-slice technique to be improved and/or simplified.

In a further embodiment, the interslice distance of the number of second slices in the navigator volume is greater than the interslice distance of the number of first slices in the reference navigator volume. This is the case when the second number of second slice groups is smaller than the first number of first slice groups. The second slices are preferably as far apart from another in the navigator volume and preferably are simultaneously positioned such that they scan the reference navigator volume as uniformly as possible.

In another embodiment, there is a first interslice distance between two adjacent second slices of a first slice pair and a second interslice distance between two adjacent second slices of a second slice pair in the navigator volume, wherein a difference between the first interslice distance and the second interslice distance is smaller than or equal to the interslice distance of the number of first slices in the reference navigator volume. This is an example of how the second slices can be distributed uniformly in the navigator volume. Thus the difference of the various interslice distances between adjacent second slices in the navigator volume is smaller than or equal to the interslice distance of the number of first slices in the reference navigator volume.

In another embodiment, the recording parameters are set to so as to cause the acquisition of magnetic resonance measurement (raw) data after the second point in time to be implemented with the movement of the examination object between the first point in time and the second point in time described in the movement information being compensated, if possible. This enables the movement of the examination object to be compensated directly during the acquisition of the magnetic resonance measurement data. Hence, a loss of signal information due to movement of the examination object can be reduced during the actual raw data acquisition.

In another embodiment, the reference navigator volume and/or the navigator volume is smaller than the examination volume for the acquisition of diagnostic magnetic resonance measurement data. The examination volume, also called field of view (FOV) represents the volume that is depicted in the image that is reconstructed form the recorded magnetic resonance measurement data. The examination volume is typically defined by a user, for example in a localizer image. The navigator volume is preferably positioned in the examination volume such that a model-based assumption, for example a model-based assumption of a rigid movement of the examination object, is satisfied as much as possible. In the case of the imaging of the head, it can be advantageous to position the navigator volume in a limited body region encompassing the base of the skull of the examination object, preferably at the rear of the base of the skull.

The magnetic resonance apparatus is designed to implement the method for movement compensation during magnetic resonance imaging of an examination object. The control computer is configured to operate the MR data acquisition scanner to perform a reference measurement at a first point in time during the magnetic resonance imaging, wherein a reference navigator volume is acquired using a simultaneous multi-slice technique with a first acceleration factor and a first number of first slice groups. The control computer is configured to operate the MR data acquisition scanner to perform a navigator measurement at a second point in time during the magnetic resonance imaging, wherein a navigator volume is acquired using a simultaneous multi-slice technique with a second acceleration factor and a second number of second slice groups, and wherein the second acceleration factor is equal to the first acceleration factor. The control computer is configured to determine movement information from the reference navigator volume and the navigator volume, wherein the movement information describes a movement of the examination object between the first point in time and the second point in time. The control computer is configured to set recording parameters of the MR data acquisition scanner after the second point in time for the further magnetic resonance raw data acquisition, dependent on the movement information.

A non-transitory, computer-readable data storage medium according to invention can be loaded directly into a memory of a programmable control computer of a magnetic resonance apparatus and is encoded with program code that causes the control computer to operate the magnetic resonance apparatus so as to implement the method according to the invention. This enables the method according to the invention to be carried out quickly, in an identically repeated way, and robustly. The computer has components such as a main memory, a graphics card or a logic unit so that the respective method steps can be carried out efficiently.

Examples for electronically readable data carriers are DVDs, magnetic tapes or USB sticks on which electronically readable control information, in particular software (see above), is stored.

The advantages of the magnetic resonance apparatus and the data storage medium according to the invention correspond to the advantages of the method according to the invention as described above in detail. Features, advantages or alternative embodiments mentioned above are also applicable to the other aspects of the invention. The functional features of the method are performed by corresponding physical modules, in particular by hardware modules.

BRIEF DESCRIPTION OF THE DRAWINGS

FIG. 1 a schematically illustrates a magnetic resonance apparatus according to the invention, FIG. 2 is a flowchart of an embodiment of a method according to the invention.

FIG. 3 is an illustration of an example of the procedure according to the invention as shown in FIG. 2.

DESCRIPTION OF THE PREFERRED EMBODIMENTS

FIG. 1 is a schematic depiction of a magnetic resonance apparatus 11 according to the invention. The magnetic resonance apparatus 11 has a data acquisition scanner 13 with a basic field magnet 17 for the generation of a strong and constant basic magnetic field 18. The scanner 13 also has a cylindrical patient reception area 14 for receiving an examination object 15, in the present case a patient, wherein the patient reception area 14 is cylindrically enclosed circumferentially by the scanner 13 in a cylindrical shape. The patient 15 can be moved into the patient reception area 14 by a patient support 16 of the magnetic resonance scanner 13. To this end, the patient support 16 has a table arranged in a movable manner within the magnetic resonance scanner 13. The scanner 13 is screened from the outside by a housing shell 31.

The scanner 13 also has a gradient coil arrangement 19 for generating magnetic field gradients, which are used for spatial encoding during imaging. The gradient coil arrangement 19 is actuated by a gradient control processor 28. The scanner 13 also has a radio-frequency (RF) antenna 20, which, in the case shown, is formed as a body coil firmly integrated in the magnetic resonance scanner 13. The radio-frequency antenna 20 is operated by the radio-frequency control processor 29 and so as to radiate radio-frequency magnetic resonance sequences into an examination chamber, which is formed by the patient reception area 14. The emitted radio-frequency sequence excites nuclear spins in the patient 15 so as to cause the nuclear spins to deviate from the polarization produced by the basic magnetic field 18 and, during relaxation thereof, the excited nuclear spins emit radio-frequency signals (magnetic resonance signals). The radio-frequency antenna unit 20 can be designed to receive the magnetic resonance signals from the patient 15 that original from the nuclear spins after excitation thereof. Alternatively one or more local RF coils can be provided for such reception.

To control the basic field magnet 17, the gradient control processor 28 and the radio-frequency control processor 29, the magnetic resonance apparatus 11 comprises a computer 24. The computer 24 is configured for central control of the magnetic resonance apparatus 11, such as the performance of a predetermined gradient echo sequence. Control information such as imaging parameters, as well as reconstructed magnetic resonance images, can be made available to a user via an output interface 25, in the present case a display monitor 25, of the magnetic resonance apparatus 11. The magnetic resonance apparatus 11 also has an input interface 26 via which information and/or parameters can be entered by a user during an examination. The computer 24 can include the gradient control processor 28 and/or the radio-frequency control processor 29 and/or the output interface 25 and/or the input interface 26.

In the case shown, the computer 24 has a determination processor 33 and a setting processor 34.

The magnetic resonance scanner 13, operated by the computer 24, serves as a reference measurement unit and a navigator measurement unit. Hence, the magnetic resonance scanner 13 is designed together with the computer 24 to execute the method according to the invention for movement compensation during magnetic resonance imaging.

The magnetic resonance apparatus 11 can have further components that are typically present in magnetic resonance apparatuses. The basic operation of a magnetic resonance apparatus 11 is known to those skilled in the art so that a more detailed description of such operation is not necessary herein.

FIG. 2 is a flowchart of a first embodiment of the method according to the invention for movement compensation during magnetic resonance imaging of an examination object 15 by operation of the magnetic resonance apparatus 11.

In a first method step 40, a reference measurement is performed at a first point in time during the magnetic resonance raw data acquisition by the scanner 13, wherein a reference navigator volume REF is acquired using a simultaneous multi-slice technique with a first acceleration factor and a first number of first slice groups A, B, C, D, E.

This method step 40 is illustrated in FIG. 3 in a segment 50. Here, the situation at the first point in time is shown schematically in an exemplary depiction. Diagnostic magnetic resonance measurement data of a head region of the examination object 15 are to be recorded by execution of a magnetic resonance sequence with a first examination volume FOV1. In this case, the first examination volume FOV1 includes the entire head of the examination object 15, which is to be depicted.

The reference navigator volume REF is now acquired at the first point in time, such as before the start or at the start of the magnetic resonance sequence. In the case shown in FIG. 3, the reference navigator volume REF is smaller than the first examination volume FOV1. In the case shown in FIG. 3, the reference navigator volume REF is positioned at an advantageous position in the examination object 15, namely in an upper head region of the examination object 15. Here, it is in particular possible to justify the assumption of a rigid movement of the examination object 15.

In the case shown, the reference navigator volume REF comprises fifteen first slices A1, B1, C1, D1, E1, A2, B2, C2, D2, E2, A3, B3, C3, D3, E3 (hereinafter: A1, B1, . . . , E3 for short), which are grouped to form five first slice groups A, B, C, D, E. In this case, a first slice group A of the five first slice groups A, B, C, D, E has three first slices A1, A2, A3 of the fifteen first slices A1, B1, . . . , E3. In the same way, each of the five first slice groups A, B, C, D, E has respective three first slices A1, B1, . . . , E3. The respective first slices A1, B1, . . . , E3 belonging to a first slice group A, B, C, D, E are measured simultaneously during the measurement of the reference navigator volume REF and to this end excited by an excitation pulse. Thus, in the case shown in FIG. 3, as an example, the reference navigator volume REF is acquired by execution of a simultaneous multi-slice technique with a first acceleration factor of three and a first number of first slice groups A, B, C, D, E of five. The number of first slices A1, B1, . . . , E3 of the reference navigator volume REF is obtained from the product of the first acceleration factor and the first number of first slice groups A, B, C, D, E and is in the case shown is therefore fifteen, as an example.

In this case, the sequence of recording of the first slices A1, B1, . . . , E3 of the reference navigator volume REF can be interleaved. Thus, slice groups A, B, C, D, E of the reference navigator volume REF that have directly adjacent first slices A1, B1, . . . , E3 are never recorded directly recorded one after the other. An example of interleaved acquisition of the reference navigator volume REF can be initially to simultaneously acquire the first slices A1, A2, A3 of the first slice group A, then the first slices C1, C2, C3 of the third slice group C, then the first slices E1, E2, . . . , E3 of the fifth slice group E, then the first slices B1, B2, B3 of the second slice group B and then the first slices D1, D2, D3 of the fourth slice group D. This enables interactions (cross-talk) between the first slices A1, B1, . . . , E3 to be reduced and/or avoided during the acquisition.

In a further method step 41, a navigator measurement is performed at a second point in time during the magnetic resonance imaging by operation of the scanner 13, wherein a navigator volume VOL is acquired using a simultaneous multi-slice technique with a second acceleration factor and a second number of second slice groups A', C' is acquired, wherein the second acceleration factor is equal to the first acceleration factor.

This method step 41 is illustrated in FIG. 3 in a segment 51. Here, the situation at the second point in time is shown schematically in an exemplary depiction. In addition, diagnostic magnetic resonance measurement (raw) data of a head region of the examination object 15 are to be recorded by execution of a magnetic resonance sequence with a first examination volume FOV1. However, the examination object 15 has moved or tilted his her head between the first point in time and the second point in time, i.e. between the situation according to segment 50 and the situation according to segment 51. Thus, the first examination volume FOV1 is no longer depicted optimally in order to acquire magnetic resonance measurement (raw) data of the tilted head.

The navigator volume VOL is now acquired at the second point in time, such as during the magnetic resonance sequence. The navigator volume VOL is positioned and/or aligned similarly to the reference navigator volume REF.

In the case shown, the reference navigator volume REF comprises six second slices A1 C1', A2', C2', A3', C3' (hereinafter: A1', C1', . . . , C3' for short), which are grouped together to form two second slice groups A', C'. At the same time, a second slice group A' of the two second slice groups A', C' comprises three second slices A1', A2', A3'. At the same time, a further second slice group C' of the two second slice groups A', C' has the three other second slices C1', C2', C3'. The respective second slices A1 C1', . . . , C3' belonging to a second slice group A', C' simultaneously measured during the measurement of the navigator volume VOL and to this end excited by execution of an excitation pulse. Thus, in the case shown in FIG. 3, the navigator volume VOL is by way of example acquired by means of a simultaneous multi-slice technique with a second acceleration factor of three and a second number of second slice groups A', C' of two. The number of second slices A1', C1', . . . , C3' of the navigator volume VOL is obtained from the product of the second acceleration factor and the second number of second slice groups A', C' and is therefore six, in the example shown.

Compared to the acquisition of the reference navigator volume REF, the acceleration factor used on the acquisition of the navigator volume VOL remains constant. Only the number of slice groups is reduced on the acquisition of the navigator volume VOL compared to the acquisition of the reference navigator volume REF. Thus, in the case shown, the second number of second slice groups A', C' is smaller than the first number of first slice groups A, B, C, D, E. In the case shown, the second number of second slice groups A', C' is even less than half the size of the first number of first slice groups A, B, C, D, E.

Furthermore, the second slice groups A', C' represent a subset of the first slice groups A, B, C, D, E. The second slices A1', C', A2', C2', A3', C3' are consequently aligned and arranged in exactly the same way as the corresponding first slices A1, C1, A2, C2, A3, C3. Consequently, no change was made to the slice parameters of the second slices A1', C1', A2', C2', A3', C3' of the navigator volume VOL compared to the corresponding first slices A1, C1, A2, C2, A3, C3 of the reference navigator volume REF. Only the number of acquired second slice groups A', C' or second slices A1', C1', . . . , C3' is reduced compared to the number of acquired first slice groups A, B, C, D, E or first slices A1, B1, . . . , C3.

Furthermore, in the case shown in FIG. 3, the second slice groups A', C' were selected such that the imaging volume covered by the navigator volume VOL is substantially the same size as the reference navigator volume REF. In particular, the second slice groups A', C' were selected such that the plurality of second slices A1', C1', . . . , C3' in the navigator volume VOL are positioned as far away as possible from one another. Hence, an interslice distance of the plurality of second slices A1', C1', . . . , C3' in the navigator volume VOL is greater than an interslice distance of the plurality of first slices A1, B1, . . . , C3 in the reference navigator volume REF.

Simultaneously, in the navigator volume VOL, there is a first distance between two adjacent second slices A1', C1', . . . , C3' of a first slice pair and a second distance between two adjacent second slices A1', C1', . . . , C3' of a second slice pair, wherein a difference between the first distance and the second distance is smaller than or equal to an interslice distance of the plurality of first slices A1, B1, . . . , C3 in the reference navigator volume REF. If, for example, the second slices A1' and C1' are considered to be the first slice pair and the second slices C2' and A3' to be the second slice pair, the first distance between the second slices A1', C1' of the first slice pair in the unit of the interslice distance of first slices A1, B1, . . . , C3 is two and the second distance between the second slices C2', A3' of the second slice pair in this unit is three. Thus, the difference between the first distance and the second distance in this unit is one and hence equal to the interslice distance of the first slices A1, B1, . . . , C3.

In a further method step 42, movement information is determined from the reference navigator volume REF and the navigator volume VOL by determination unit 33, wherein the movement information describes a movement of the examination object 15 between the first point in time and the second point in time. The movement information can be determined, for example, by a registration of the acquired navigator volumes VOL to the reference navigator volume REF. Other possibilities for the determination of the movement information from the navigator volume VOL and the reference navigator volume REF that are reasonable to those skilled in the art are also conceivable.

In the case shown in FIG. 3, a head movement of the examination object 15 has occurred between the first point in time shown in the segment 50 and the second point in time shown in the segment 51. For example, the examination object 15 has tilted his or her head so that, at the second point in time, the first examination volume 15 no longer depicts the head of the examination object 15 to the optimum degree. The movement information determined from the reference navigator volume REF and the navigator volume VOL is able to describe this tilting of the head, for example from the rotation parameters and/or translation parameters determined.

In a further method step 43, recording parameters are set. This setting of recording parameters occurs after the second point in time for the magnetic resonance raw data acquisition, as a function of the movement information, by the setting processor 34. In this case, the setting of the recording parameters can take place such that the acquisition of magnetic resonance measurement data during the magnetic resonance imaging after the second point in time is performed such that the movement of the examination object 15 between the first point in time and the second point in time described in the movement information is compensated if possible.

In the case shown in FIG. 3, segment 52, which represents the period after the second point in time, displays a second examination volume FOV2 adapted using the movement information, which is tilted compared to the first examination volume FOV1 according to the movement of the head of the examination object 15. This enables the second examination volume FOV2 to depict the head region of the examination object 15 in an optimal manner.

In this case, the magnetic resonance measurement data represent diagnostic magnetic resonance measurement data. In this case, the diagnostic magnetic resonance measurement data can be acquired by execution of a known magnetic resonance sequence for the magnetic resonance raw data acquisition. The magnetic resonance measurement data are used for the reconstruction of magnetic resonance image data which can be made available, i.e. displayed to a user on the display monitor of the output interface 25, and/or stored in a database. In this case, the magnetic resonance measurement data can be acquired from an examination volume FOV1, FOV2, wherein the reference navigator volume REF and/or the navigator volume VOL is advantageously smaller than the examination volume FOV1, FOV2.

The method steps of the method according to the invention shown in FIG. 2 are executed in the computer 24. To this end, the computer 24 has the necessary software and/or computer programs, which are stored in a memory of the computer 24. The software and/or computer programs have program code designed to cause the method according to the invention to be implemented when the code is executed in the computer 24 by means of one or more processors of the computer 24.

The illustration of the procedure according to the invention shown in FIG. 3 is only an example. It is also possible to use a different acceleration factor, different numbers of slice groups or slices, different positions or alignments of slices. It is also obviously possible to examine another body region of the examination object 15. It is also possible to compensate another movement of the examination object 15, for example a respiratory movement.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a magnetic resonance (MR) apparatus, said method comprising:
   from a computer providing control signals in an MR operating sequence to an MR data acquisition scanner so as to operate said MR data acquisition, at a first point in time during said MR operating sequence, to acquire MR navigator data from a reference navigator volume of an examination object using a simultaneous multi-slice data acquisition technique with a first acceleration factor and a first number of first slice groups;
   from said control computer, operating said MR data acquisition scanner with said control signals at a second point in time during said MR operating sequence without acquiring MR raw data between said first and second points in time, in order to acquire further MR navigator data from a navigator volume of the examination object at said second point in time using a simultaneous multi-slice technique with a second acceleration factor and a second number of second slice groups, with said second acceleration factor being equal to said first acceleration factor;
   receiving the MR navigator data from the reference navigator volume and the further MR navigator data from the navigator volume at said computer and, in said computer, determining movement information from said reference navigator volume and said navigator volume that describes a movement of said examination object between said first point in time and said second point in time;
   generating movement-dependent raw data acquisition parameters in said computer from said movement information; and
   in said computer, generating MR raw data acquisition control signals representing said movement-dependent raw data acquisition parameters, and providing MR data acquisition control signals in electronic form from said computer to said MR data acquisition scanner and thereby setting said movement-dependent data acquisition parameters in said MR data acquisition scanner, after said second point in time, and thereafter operating said MR data acquisition scanner, also in said MR operating sequence, with said movement-dependent data acquisition parameters to acquire MR raw data, from which a diagnostic image can be reconstructed, from the examination object after said second point in time.

2. A method as claimed in claim 1 comprising acquiring said further MR navigator data representing said navigator volume with said second number of second slice groups being smaller than said first number of first slice groups.

3. A method as claimed in claim 2 wherein said second number of slice groups is less than half of said first number of first slice groups.

4. A method as claimed in claim 1 comprising acquiring said further MR navigator data representing said navigator volume with said second slice groups being a subset of said first slice groups.

5. A method as claimed in claim 1 comprising acquiring said further MR navigator data representing said navigator volume with said second slice groups being selected to cause a volume encompassed by said navigator volume to be substantially equal to said reference navigator volume.

6. A method as claimed in claim 1 comprising acquiring said MR navigator data representing said reference navigator volume from a plurality of first slices and grouping said plurality of first slices together to form said first slice groups, and acquiring said further MR navigator data representing said navigator volume from a plurality of second slices, and grouping said plurality of second slices together to form said second slice groups.

7. A method as claimed in claim 6 comprising selecting said second slice groups to cause said plurality of second slices to be positioned in said navigator volume as far from each other as possible.

8. A method as claimed in claim 6 wherein said plurality of first slices have a first interslice distance therebetween in said reference navigator volume, and wherein said plurality of second slices have a second interslice distance therebetween in said navigator volume, and selecting said plurality of second slices to cause said second interslice distance to be greater than said first interslice distance.

9. A method as claimed in claim 6 comprising selecting said plurality of second slices with a first interslice distance between two adjacent second slices of a first slice pair among said plurality of second slices, and with a second interslice distance between two adjacent second slices of a second slice pair among said plurality of second slices, with a difference between said first interslice distance and said second interslice distance being less than or equal to an interslice distance between said plurality of first slices in said reference navigator volume.

10. A method as claimed in claim 1 comprising setting said movement-dependent data acquisition parameters of said MR scanner to cause said MR raw data acquired after said second point in time to compensate for said movement described in said movement information.

11. A method as claimed in claim 1 comprising acquiring said MR raw data in said MR operating sequence from an examination volume of the examination object, and selecting at least one of said reference navigator volume and said navigator volume to be smaller than said examination volume.

12. A magnetic resonance (MR) apparatus comprising:
an MR data acquisition scanner;
a control computer configured to operate the MR data acquisition scanner so as to execute an MR operating sequence to obtain raw MR data from an examination object while the examination object is situated in the MR scanner;
said control computer being configured to operate said MR data acquisition scanner, at a first point in time during said MR operating sequence, to acquire MR navigator data from a reference navigator volume of the examination object using a simultaneous multi-slice data acquisition technique with a first acceleration factor and a first number of first slice groups;
said control computer being configured to operate said MR data acquisition scanner at a second point in time during said MR operating sequence without acquiring MR raw data between said first and second points in time, in order to acquire MR data from a navigator volume of the examination object at said second point in time using a simultaneous multi-slice technique with a second acceleration factor and a second number of second slice groups, with said second acceleration factor being equal to said first acceleration factor;
said control computer being configured to determine movement information from said reference navigator volume and said navigator volume that describes a movement of said examination object between said first point in time and said second point in time;
said control computer being configured to generate movement-dependent raw data acquisition parameters from said movement information; and
said control computer being configured to generate MR raw data acquisition control signals representing said movement-dependent raw said data acquisition, and to provide MR data acquisition control signals parameters from said computer to said MR data acquisition scanner and thereby set said movement-dependent data acquisition parameters in said MR data acquisition scanner, after said second point in time, and thereafter operate said MR data acquisition scanner, also in said MR operating sequence, with said movement-dependent data acquisition parameters to acquire MR raw data, from which a diagnostic image can be reconstructed, from the examination object after said second point in time.

13. A non-transitory, computer-readable data storage medium encoded with programming instructions, said data storage medium being loaded into a control computer of a magnetic resonance (MR) apparatus that comprises an MR data acquisition scanner, and said programming instructions causing said control computer to:
generate control signals to operate the MR data acquisition scanner so as to execute an MR operating sequence;
operate said MR data acquisition scanner with said control signals, at a first point in time during said MR operating sequence, to acquire MR navigator data from a reference navigator volume of the examination object using a simultaneous multi-slice data acquisition technique with a first acceleration factor and a first number of first slice groups;
operate said MR data acquisition scanner with said control signals at a second point in time during said MR operating sequence without acquiring MR raw data between said first and second points in time, in order to acquire further MR navigator data from a navigator volume of the examination object at said second point in time using a simultaneous multi-slice technique with a second acceleration factor and a second number of second slice groups, with said second acceleration factor being equal to said first acceleration factor;
determine movement information from said navigator data from said reference navigator volume and from said further navigator data from said navigator volume that describes a movement of said examination object between said first point in time and said second point in time;
generate movement-dependent data acquisition parameters from said movement information; and
generate MR raw data acquisition control signals representing said movement-dependent raw data acquisition parameters, and provide MR data acquisition control signals from said computer to said MR data acquisition scanner and thereby set said movement-dependent data acquisition parameters in said MR data acquisition scanner, after said second point in time, and thereafter operate said MR data acquisition scanner, also in said MR operating sequence, with said movement-dependent data acquisition parameters to acquire MR raw data, from which a diagnostic image can be reconstructed, from the examination object after said second point in time.

* * * * *